(12) United States Patent
Ye et al.

(10) Patent No.: US 8,781,603 B2
(45) Date of Patent: Jul. 15, 2014

(54) MINIMALLY INVASIVE METHODS FOR IMPLANTING A SACRAL STIMULATION LEAD

(71) Applicant: Greatbatch Ltd., Clarence, NY (US)

(72) Inventors: Qingshan Ye, Plymouth, MN (US); John M. Swoyer, Blaine, MN (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 14/033,592

(22) Filed: Sep. 23, 2013

(65) Prior Publication Data
US 2014/0031909 A1  Jan. 30, 2014

Related U.S. Application Data

(62) Division of application No. 12/506,282, filed on Jul. 21, 2009, now Pat. No. 8,634,932.

(60) Provisional application No. 61/082,271, filed on Jul. 21, 2008.

(51) Int. Cl.
*A61N 1/00* (2006.01)
*A61N 1/05* (2006.01)

(52) U.S. Cl.
CPC ............... *A61N 1/0558* (2013.01); *A61N 1/00* (2013.01)
USPC ........................................ 607/117

(58) Field of Classification Search
CPC ............................... A61N 1/00; A61N 1/0558
USPC .................. 607/116–117, 128; 600/377
See application file for complete search history.

(56) References Cited

U.S. PATENT DOCUMENTS

| | | | |
|---|---|---|---|
| 4,585,013 A | * | 4/1986 | Harris ............................ 607/126 |
| 4,913,164 A | | 4/1990 | Greene et al. |
| 5,380,290 A | * | 1/1995 | Makower et al. .......... 604/164.01 |
| 5,390,671 A | | 2/1995 | Lord et al. |
| 6,971,393 B1 | | 12/2005 | Mamo et al. |
| 6,999,819 B2 | | 2/2006 | Swoyer et al. |
| 7,328,068 B2 | | 2/2008 | Spinelli et al. |
| 7,328,069 B2 | | 2/2008 | Gerber |
| 7,330,764 B2 | | 2/2008 | Swoyer et al. |

* cited by examiner

*Primary Examiner* — Mark W Bockelman
(74) *Attorney, Agent, or Firm* — Michael F. Scalise

(57) ABSTRACT

Methods and apparatus for implanting a neural stimulation lead in a patient's body are described. A lead assembly comprises a pointed-tip stylet, a stimulation lead, and an optional tube to deploy a fixation element attached to the lead. One embodiment of the implant methods starts with inserting the pointed-tip lead assembly directly into tissue. After the desired implant position is determined, the pointed-tip component is separated from the stimulation lead and removed from the tissue, leaving the stimulation lead implanted. After confirmation that the stimulation lead is in the right tissue location, the pointed-tip component is removed from the body, leaving the stimulation lead in place. The stimulation lead can be connected to a neurostimulator to delivery therapies to treat neural disorders, such as urinary control disorders, fecal control disorders, sexual dysfunction, and pelvic pain, etc.

20 Claims, 10 Drawing Sheets

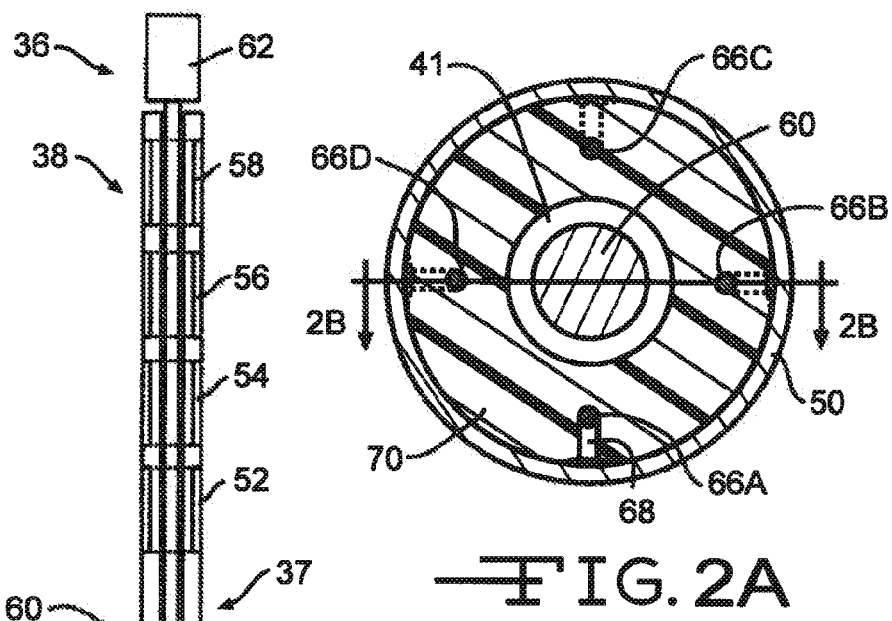
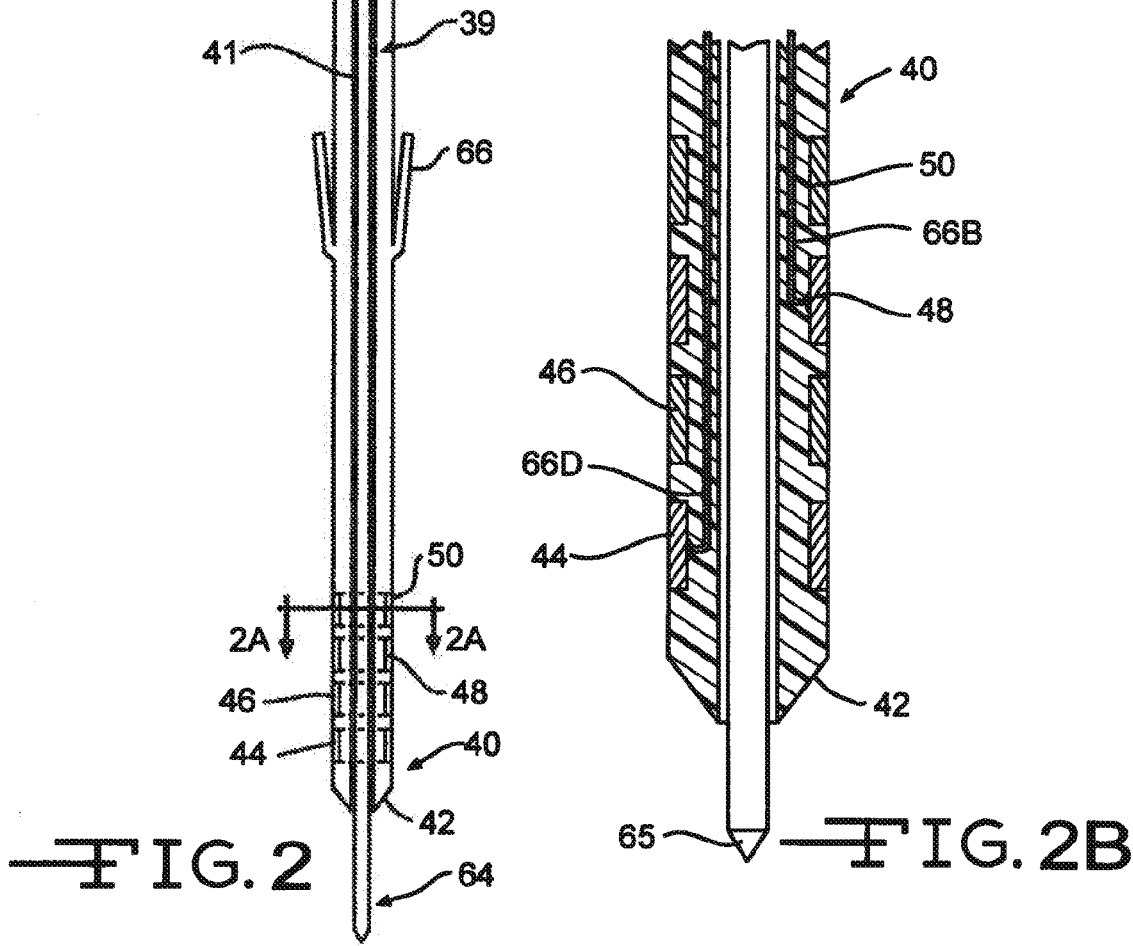

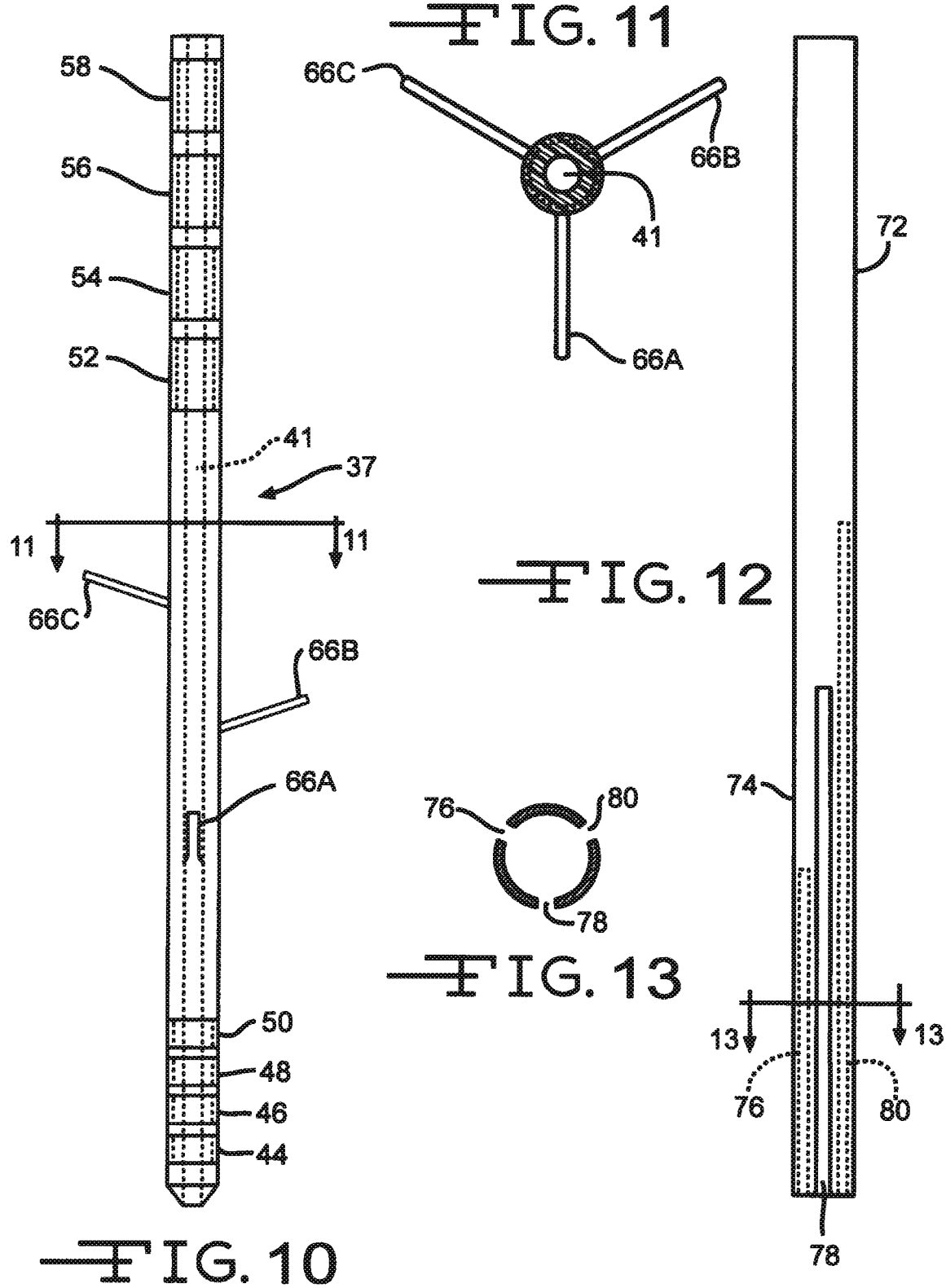

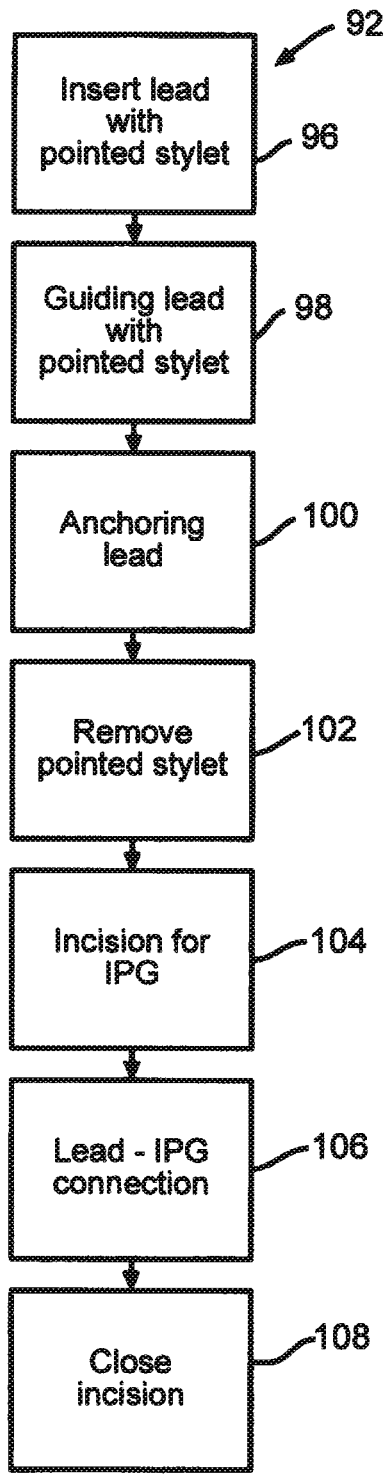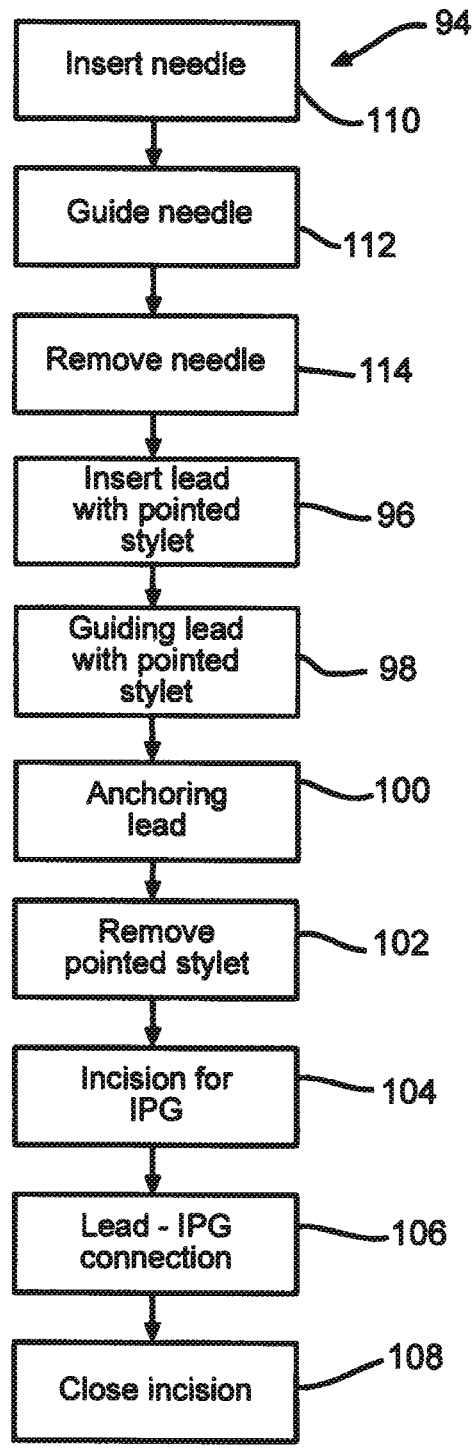

MINIMALLY INVASIVE METHODS FOR IMPLANTING A SACRAL STIMULATION LEAD

CROSS-REFERENCE TO RELATED APPLICATIONS

This application is a divisional of U.S. patent application Ser. No 12/506,282, filed on Jul. 21, 2009, which claims priority from U.S. Provisional Application Ser. No. 61/082, 271, filed Jul. 21, 2008.

TECHNICAL FIELD

The present invention relates to a neural stimulation lead assembly and minimally invasive implant methods associated with use of the described lead assembly. More specifically, the present invention relates to a lead assembly including a stimulation lead and a pointed-tip stylet received in a lumen of the lead. Minimally invasive method involves inserting the lead assembly into tissue without using a dilator.

BACKGROUND OF THE INVENTION

Many people suffer from an inability to control urinary function, i.e., urinary incontinence. Different muscles, nerves, organs and conduits within the urinary tract cooperate to collect, store and release urine. A variety of disorders may compromise urinary tract performance and contribute to incontinence. Many of the disorders may be associated with aging, injury or illness. For example, aging can often result in weakened sphincter muscles, which cause incontinence, or weakened bladder muscles, which prevent complete emptying. Some patients also may suffer from nerve disorders that prevent proper triggering and operation of the bladder or sphincter muscles.

Fecal incontinence is the inability to control bowel function. Fecal incontinence may be attributable to many physiological conditions, such as damage to the muscles of the rectum (e.g., the anal internal or external sphincters), nerve damage, loss of storage capacity within the rectum, and pelvic floor dysfunction.

Electrical stimulation of nerves may provide an effective therapy for a variety of disorders, including urinary incontinence and fecal incontinence. For example, an implantable neurostimulator can deliver electrical stimulation to the sacral nerve to induce sphincter constriction and thereby close or maintain closure of the urethra at the bladder neck. In addition, electrical stimulation of the bladder wall may enhance pelvic floor muscle tone and assist fluid retention in the bladder or voiding fluid from the bladder.

In current clinical practice to minimally implant a sacral stimulation lead, the procedure starts with a kit comprising a needle and a dilator that are particularly adapted to enable introduction of a neurostimulation lead into a foramen to locate a distal lead electrode(s) in operative relation to a sacral nerve. The needle is adapted to be inserted through an entry point of the skin or a skin incision posterior to the sacrum. The needle is guided along an insertion path into a foramen to locate at least a distal portion thereof extending alongside a sacral nerve. A proximal portion of the needle extends from the entry point away from the patient's skin. The dilator is inserted over the needle proximal end and advanced distally over the needle to dilate the insertion path to that of the dilator diameter. The needle is then withdrawn through the dilator body lumen. The stimulation lead can now be advanced through the dilator body lumen to locate the lead electrode into operative relation with the sacral nerve. The dilator is then withdrawn over or removed from the stimulation lead body.

The above practice requires multiple steps and disposable components in a kit to implant the stimulation lead. This takes time and creates extra trauma around the stimulation lead. Therefore, in the current invention, a simplified implant method, and a modified stimulation lead and kit are described.

SUMMARY OF THE INVENTION

A minimally invasive implant method starts with inserting a pointed-tip lead assembly directly into tissue. The desired implant position is determined by electric stimulation either through the stimulation lead or the pointed tip. Afterwards, the pointed-tip component is separated from the stimulation lead and removed from the tissue, leaving the stimulation lead implanted. In one variation, a needle is first inserted to identify the optimal stimulation site. After marking the needle path and position, the needle is removed and a pointed-tip stimulation lead assembly is inserted along the marked needle path. After confirmation that the stimulation lead is in the right tissue location, the pointed-tip component of the lead assembly is removed from the body, leaving only the stimulation lead in place. This minimally invasive implant method can be practiced in a wide variety of neural stimulation applications, including sacral nerve stimulation.

BRIEF DESCRIPTION OF THE DRAWINGS

FIG. 2 shows a lengthwise cross-section view of stimulation lead assembly, with the proximal end of the pointed-stylet attached to the stimulation proximal end via a cap.

FIG. 2A is a cross-sectional view taken along line 2A-2A of FIG. 2

FIG. 2B is a cross-sectional view taken along line 2B-2B of FIG. 2A.

FIG. 10 shows a stimulation lead design with multiple fixation elements attached at different locations along the lead intermediate section.

FIG. 11 shows a cross-section view taken along line 11-11 of FIG. 10.

FIG. 12 shows an activation tube used to deploy the fixation elements shown in FIG. 10.

FIG. 13 shows a cross-sectional view along line 13-13 of FIG. 12.

FIG. 22 is a flowchart of a first minimally invasive method embodiment.

FIG. 23 is a flowchart of a second minimally invasive method embodiment.

DESCRIPTION OF THE PREFERRED EMBODIMENTS

Figure 1:
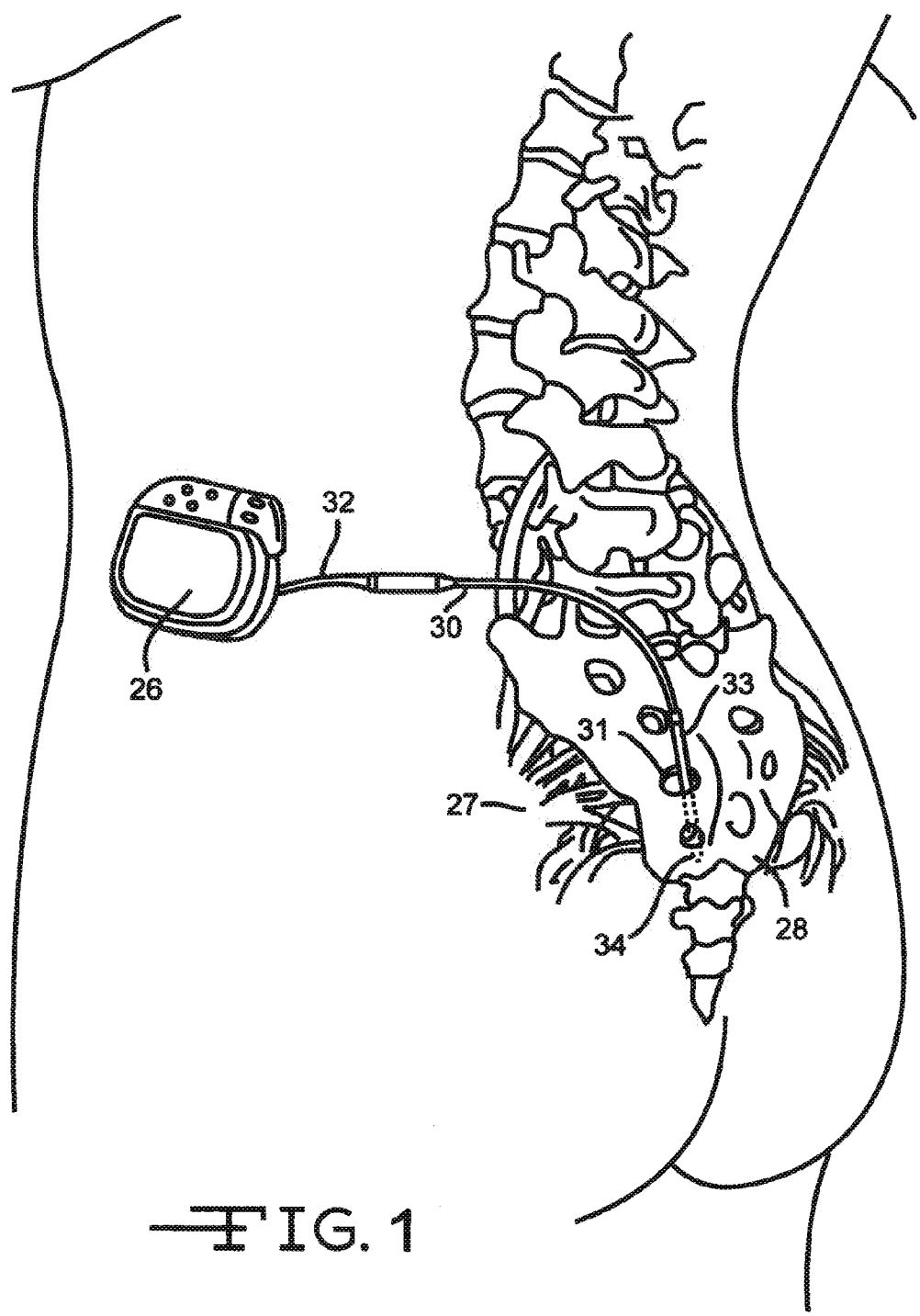
FIG. 1 shows an embodiment of an implanted neurostimulator.

FIG. 1 shows an embodiment of an implanted neurostimulator 26 for stimulating sacral nerves 27 located near the sacrum 28. The sacral nerves are accessible through an entry point, in the skin along an insertion path 33 into a foramen 31 to reach a desired location 35. A neurostimulation system can include a stimulation lead 30, an optional lead extension 32, an implantable neurostimulator 26, a physician programmer (not shown), and a patient programmer (not shown). The stimulation lead 30 has electrical contacts 34 positioned on the distal end to stimulate nerves, and connectors (not shown) on the proximal end to connect to a lead extension or directly to the implantable neurostimulator 26.

The implantable neurostimulator 26 provides a programmable stimulation signal that is delivered to a desired location to stimulate selected nerves. The implantable neurostimulator 26 is typically implanted in a subcutaneous pocket around the upper buttocks, sometime after the stimulation lead 30 has been implanted and its effectiveness verified. The physician programmer is used by the clinician to program the stimulation signal produced by the implantable neurostimulator 26. The patient programmer allows the patient to communicate with the implantable neurostimulator to control certain parameters of the stimulation signal typically selected by a clinician. For example, with a pelvic floor disorder, a patient can typically control stimulation signal parameters such as voltage amplitude.

As a preferred embodiment of the current invention, FIG. 2 shows a lead assembly 36 comprising a stimulation lead 37 and a pointed tip stylet 60. The stimulation lead 37 has a proximal portion 38, a distal portion 40 and an intermediate portion 39. As one of the preferred embodiments, the distal portion has four electrical contacts 44, 46, 48 and 50 serving as stimulation electrodes. These contacts can be made of iridium/platinum alloy rings. The lead proximal portion also has four electrical connectors 52, 54, 56 and 58 for connecting the lead proximal portion 38 to the neurostimulator 26. These electric connectors can be made of stainless steel rings.

Figure 3:
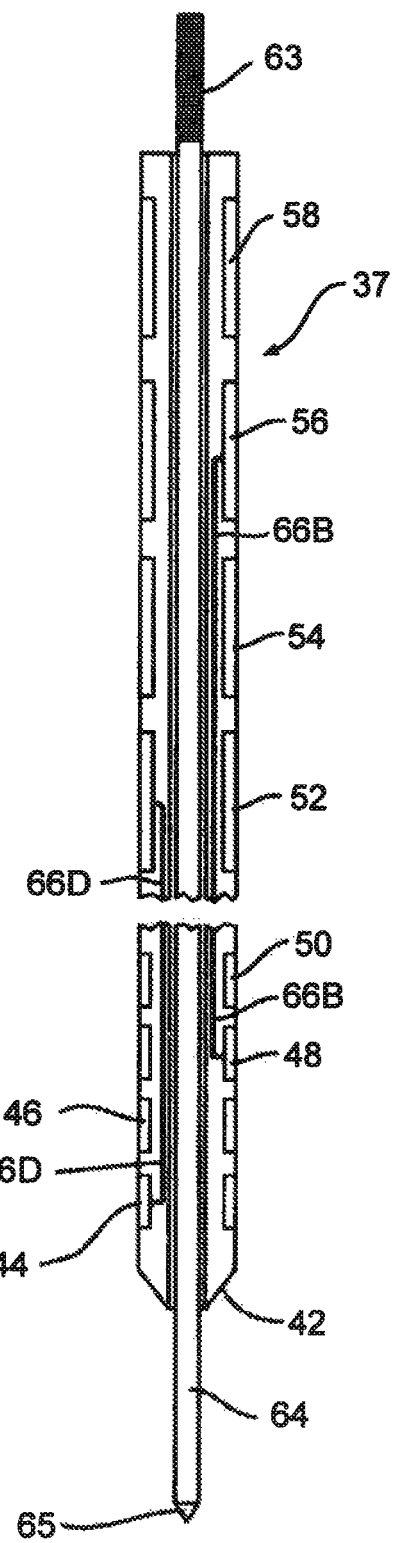
FIG. 3 shows the proximal end of the stylet uncoupled from stimulation lead of FIG. 2 by removing the cap.

Electric pulses from the neurostimulator 26 run through the proximal connectors 52, 54, 56 and 58 and along the lead body to the distal electrodes 44, 46, 48 and 50 via respective electrical wires 61A, 61B, 61C and 61D (FIG. 2A). For example, as shown in FIGS. 2, 2B and 3, the distal electrode 44 is connected by wire 66D to the proximal connector 52 and electrode 48 is connected by wire 66B to the proximal connector 56. These wires are embedded in the lead insulation body 70 (FIG. 2A). The connection of a wire at its ends to a distal electrode and a proximal connector can be achieved by various means, for example, laser welding. This is shown in FIG. 2A where a laser welded connection 68 links wire 61A to electrode 50.

Typically the insulation portion of the lead body is made of biocompatible silicone or polyurethane. As shown in FIGS. 2 and 3, the proximal connectors 52, 54, 56 and 58 and distal electrodes 44, 46, 48 and 50 can be partially embedded in the lead body to form a diametric profile and to minimize trauma during lead implant. This partial embedding can be achieved by grinding or thermal reflow.

The lead body has a central lumen 41 extending from the proximal portion 38 to the distal end 40. The stylet 60 runs through the central lumen thereof. The stylet 60 has a distal end 64 with a pointed tip 65. In use, the distal end 64 extends out of the lead body a sufficient distance to expose the pointed tip 65. The stylet 60 also has a coupling element 62 at its proximal portion 63 that couples with the lead proximal portion 38. As shown in FIG. 2, this coupling element 62 can be a removable cap attached at the stylet proximal end 63. As a variation in a preferred embodiment, this coupling element can also be removably attached to the stylet proximal end 63 and lead proximal portion 38, for example a clamp holding the lead and the stylet together.

During insertion of the lead assembly 36 into tissue, the coupling element 62 helps prevent stylet movement inside the lumen 41. That is so the lead assembly 36 can be inserted as a single unit by holding both its intermediate portion 39 and optionally its proximal portion 38.

As shown in FIG. 3, after the lead 36 assembly is inserted into tissue, the coupling element 62 is removed and the stylet 60 moved back and forth within the central lumen 41 by pulling or pushing its proximal end against the lead proximal portion 38. The stlyet 60 can be made of metal that is electrically conductive. That is so electric pulses can be fed from its proximal end into its distal end 64 where the pulses will evoke a patient motor or sensory response. To enhance the accuracy and localization during the desired stimulation site probing process, the stylet distal end can be partially insulated, for example by a thin layer of polytetrafluoroethylene (PTFE), with only the tip 65 being left exposed. By moving the pointed-tip stylet freely inside the lead central lumen 41, a desired stimulation location can be probed by the stylet 60, preferably aided by the patient motor or sensory response.

Once a desired stimulation location has been identified using the tip 65 of the stylet 60, the lead 37 is positioned close to the desired location by holding the intermediate portion 39 and pushing the lead forward over the stylet. To facilitate lead advancement through tissue over the stylet, FIG. 2B shows a tapered end 42 at the lead distal portion 40. The final location of the lead can be verified by feeding electric pulses from at least one of the lead proximal connectors 52 to 58 to at least one of the distal electrodes 44 to 50.

Once verification of the desired lead placement is complete, it is necessary to anchor the lead, for example by a fixation element build on the stimulation lead 37. This fixation element is deployed into tissue surrounding the lead. Once deployed, the fixation element prevents lead movement in both longitudinal and lateral directions.

Figure 4:
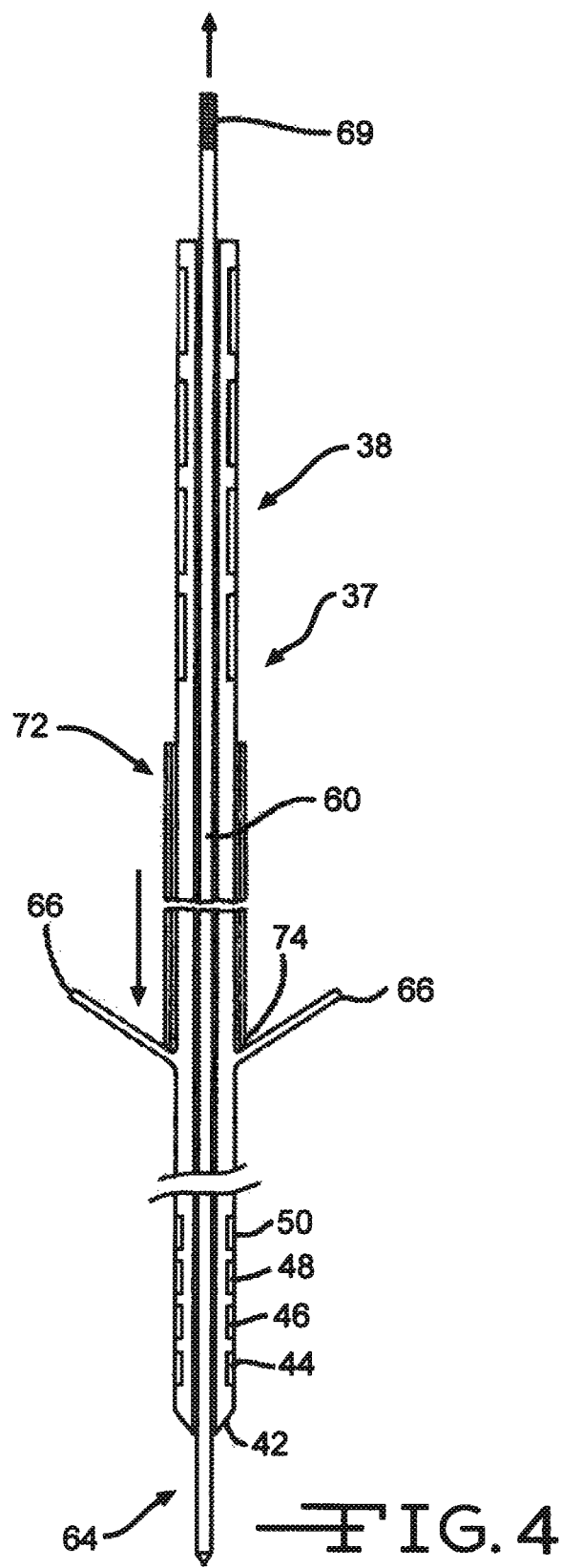
FIG. 4 shows how a tube being pushed over the lead to extend fin-type fixation elements attached at the lead intermediate section.
Figure 5:
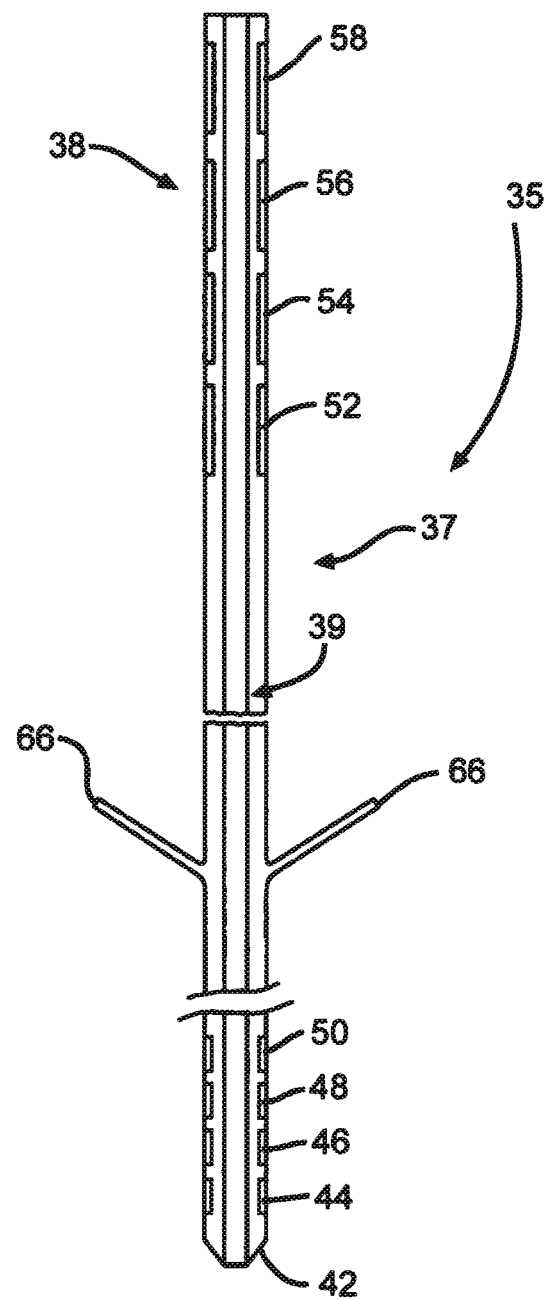
FIG. 5 shows the stimulation lead in a deployed state after separately removing the stylet and the tube used for activating the fixation elements on the lead body.
Figure 6:
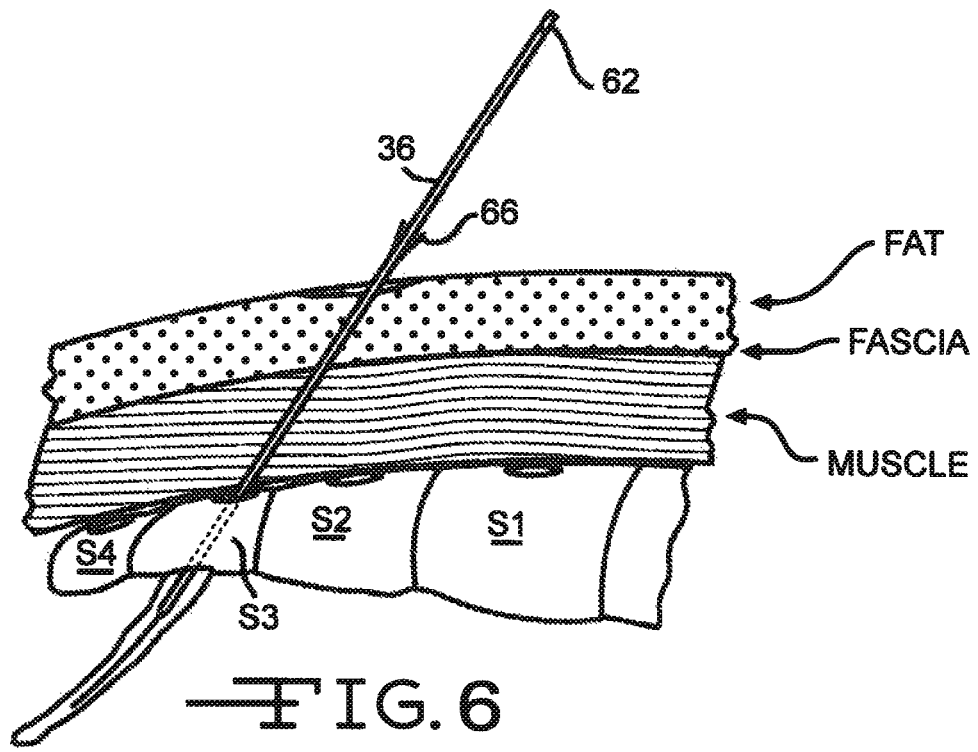
FIG. 6 shows a cross-section view of a stimulation lead assembly inserted through tissue and into a foramen, led by the pointed-tip stylet at the distal end.

As shown in FIGS. 2, 4 and 5, one preferred embodiment of a fixation element, is of a fin-like structure 66. The fins 66 are finger-like structures having an length substantially longer than their diameter or width taken along a cross-section perpendicular to the length thereof. They are preferably of an elastic material, for example, of polyurethane or silicone and only one of their ends is attached on the outer surface of the lead intermediate portion 39. Attachment can be achieved by injection molding or adhesive bonding. Before the fixation fins 66 are deployed into tissue, the opposite ends of the fins should be pointed toward the lead proximal portion 38. That is in order to reduce resistance when entering tissue during the lead insertion process. After the desired stimulation location is identified and the fixation fins 66 are ready to be deployed, a preferred embodiment of the current invention includes a tube 72 (FIG. 4). The tube 72 is positioned over the lead body and pushed down from the proximal portion 38 toward the lead intermediate portion 39 until the distal tube end 74 touches the fixation fins 66. Tube 72 first touches the non-attached ends of the fins 66 and pushes them away from the lead intermediate portion 39. This movement stops when the tube 72 contacts the attached ends of the fins 66. Thus, the fixation element is moved from its initial state (FIG. 2) into its final deployed state (FIG. 4) via tube 72. FIG. 5 shows the lead with the fixation fins 66 deployed and the tube 72 removed from the lead 37.

As a preferred embodiment of the current invention, FIGS. 6 to 9 show a minimally invasive method for implanting the above-described stimulation lead-stylet assembly 36 percutaneously. The method is also described in the flowchart of FIG. 22.

Briefly, a local anesthetic is typically applied to the area where the stimulation lead-stylet assembly 36 will be implanted, for example, posterior to the sacrum 28. By using local anesthesia, an implanting clinician can include the patient's conscious sensory responses to electric stimuli to aid in placing the stimulation lead-stylet assembly 36.

Figure 7:
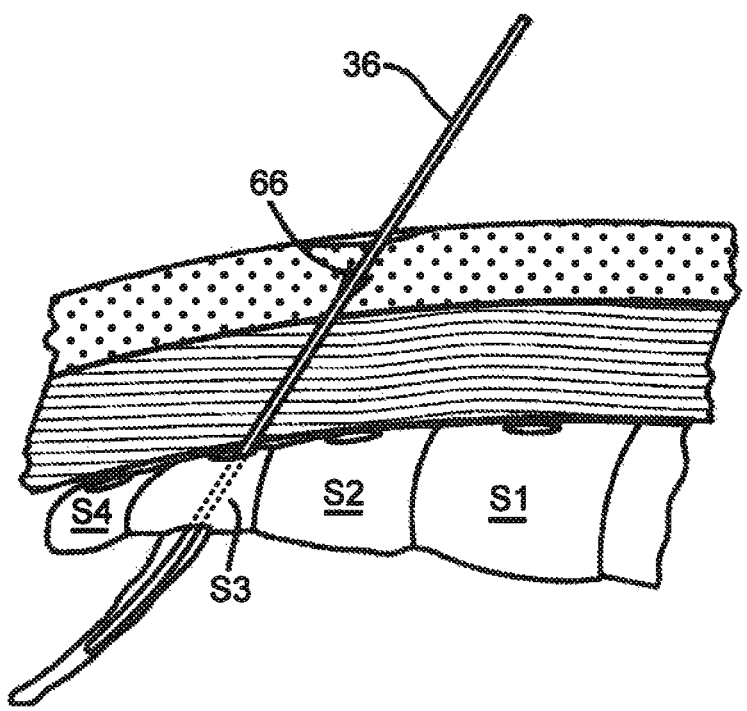
FIG. 7 shows the stylet retracted from the distal end of FIG. 6 and placement of the stimulation lead at the stimulation site.

The lead-stylet assembly 36 is hand guided 98 into the foramen 31 along an insertion path 33. The foramen's 31 approximate location can be found using anatomical landmarks, fluoroscopy or x-ray images. Once the lead-stylet assembly 36 has been placed inside the foramen 31, the coupling 62 between the stimulation lead and stylet is removed. The desired stimulation site can be first probed by the stylet and sensed by a variety of means such as by applying electric pulses to the stylet 60 at its proximal end 63 to evoke a patient response, such as a motor or sensory response. As shown in FIG. 7, once the stylet is in place, the tapered stimulation lead can be pushed over the stylet and moved into the identified stimulation site.

Before anchoring the lead with the fixation element 66 using the tube 72, however, verification of lead placement at the desired location should he made. This is done by feeding electric pulses to at least one of the lead proximal electric connectors 52, 54, 56 and 58, and sensing or stimulating by at least one of the lead distal electrodes 44 to 50.

Figure 8:
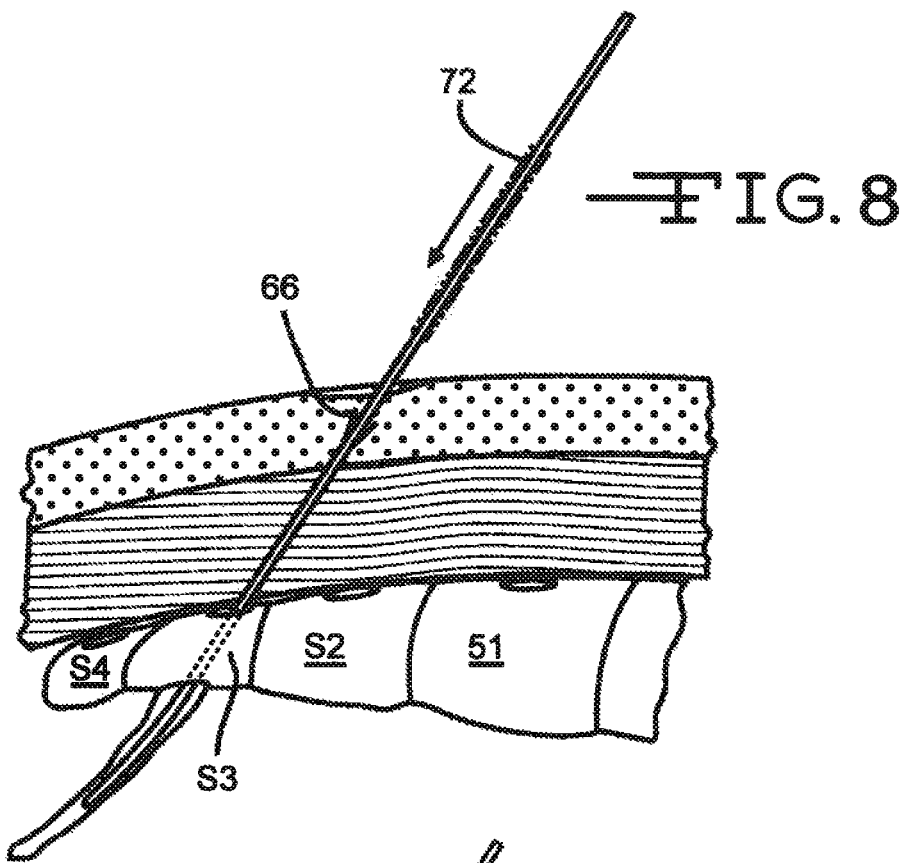
FIG. 8 shows a cross-section view of a tube being pushed over the implant lead to activate the fixation element on the intermediate portion of the lead.
Figure 9:
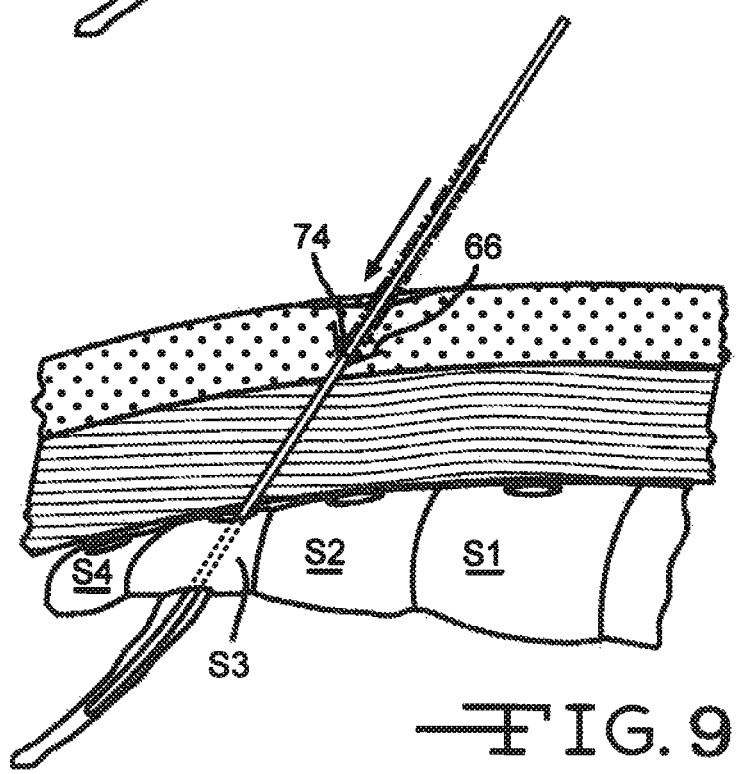
FIG. 9 is a cross-sectional view showing deployment of the fixation element in tissue by the tube.

FIGS. 8 and 9 show the step 100 of anchoring the lead 36. This is done by pushing the tube 72 over the lead-stylet assembly 36 until, the tube contacts the fixation element. 66. The force exerted by the tube distal end. 74 on the fixation fins 66 pushes their non-attached ends away from the surface of the lead intermediate portion 39 and into the tissue, preferably at a fascia layer, such as the lumbosacral fascia layer. The lubosacral fascial layer may be located at different depth from the skin for different patient. For that reason, the provision of multiple fixation fins enables the clinician to successfully deploy at least one of them at the preferred lumbosacral, layer are described.

A preferred embodiment comprising multiple fixation fins supported on a stimulation lead 37 is shown in FIG. 10. By way of example, this embodiment has three fin-like fixation elements 66A, 665 and 66C, each having only one end attached to the lead body. The opposite end of the fins extends away from the lead surface when it is deployed by tube 72 in a similar manner as shown in FIG. 4. These fixation elements can be made of material having elastic properties, such as polyurethane or silicone, and are similar to the fins 66 described in FIGS. 2, 4 and 5. However, they are attached to the lead intermediate portion 39 at different axial locations. Initially, the non-attached ends point to the lead proximal portion 38 during insertion of the lead-stylet assembly 36. Once deployed into tissue, as shown in the cross-sectional view of FIG. 11, the three fixation elements are preferably about 120 degrees from each other.

The deployment tube 72 shown in FIG. 12 has three slots 76, 78 and 80 with different lengths measured from the tube 72 distal end at the tube distal portion 74. As shown in FIG. 13, these slots are also about 120 degrees apart from each other. That is so when the tube 72 is pushed over the lead-stylet assembly 36, the length and orientation of the various slots deploys only one of the fixation fins 66A to 66C. For example, slot 76 only deploys fixation element 66A, slot 78 only deploys a respective fixation element 66B, and slot 80 only deploys fixation element 660.

Figure 14:
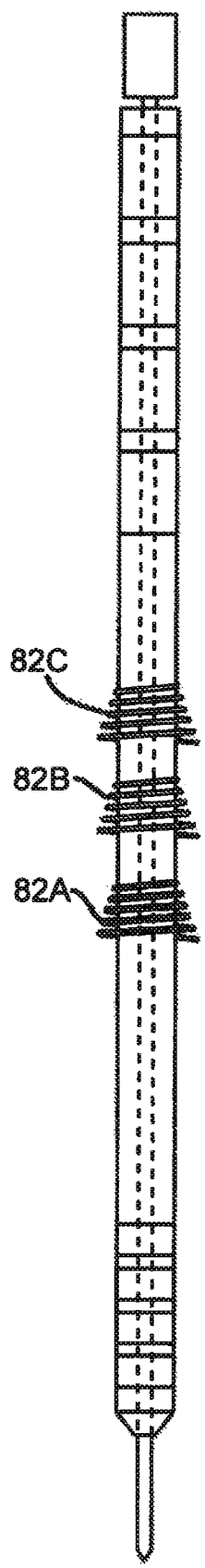
FIG. 14 shows tapered coils as fixation elements along a stimulation lead.

FIG. 14 shows another preferred embodiment of a fixation structure. In this embodiment, there are three tapered coils 82A, 82B and 82C, each having a smaller diameter end and a larger diameter end. Only the smaller diameter end is attached to the surface of the lead intermediate portion 39 with the remainder of the coil surrounding the perimeter of the lead. The tapered coils can be twisted in one direction at their larger end. This causes their larger diameters to shrink so that the coil fits into a tube 73 whose inner diameter is smaller than the coil's uncoiled diameter. The lead-stylet assembly in this case will also include the tube 73 covering only the lead intermediate portion 39 and part of lead distal portion 38 (not shown).

Figure 15:
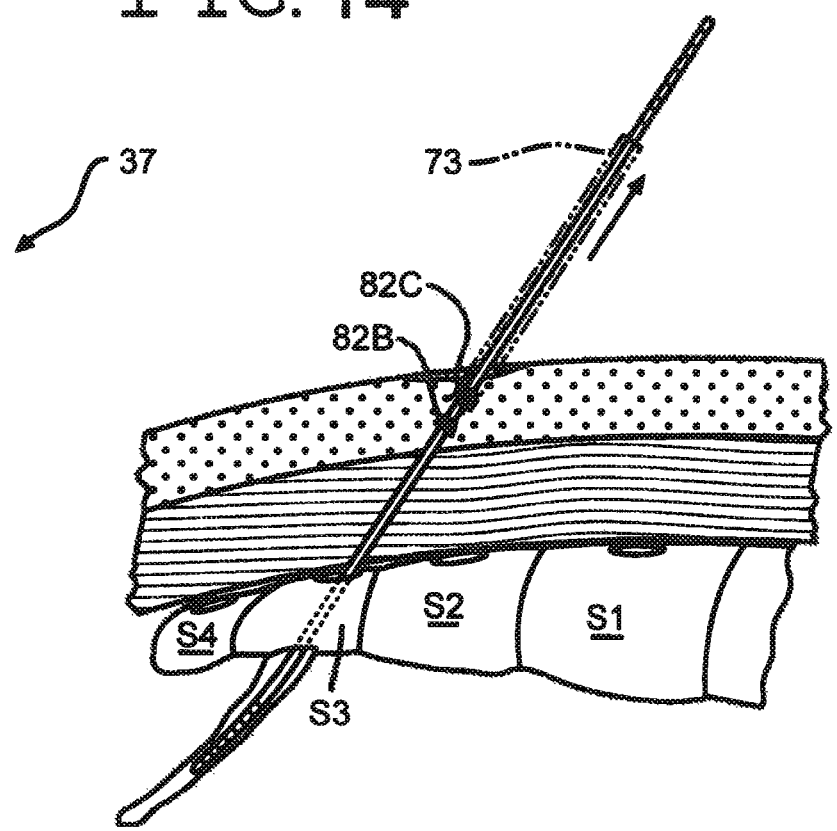
FIG. 15 shows the implant of stimulation lead assembly and deployment of tapered coil fixation in tissue.

During the implanting process shown in FIG. 15, the entire lead assembly including the tube 73 is inserted into body tissue. After the desired stimulation site has been identified by the pointed stylet 60 and the fixation elements 82A, 82B and 82C are ready to be deployed, the tube 73 is retracted from the stimulation lead. As this movement takes place, the coils are released from inside the tube 73 and expand like a torsion spring surrounding the lead. At least one of the tapered coils is preferably expanded within the lumbosacral fascial layer. These tapered coils are preferably made of biocompatible metals, such as stainless steel, platinum, titanium, NP35N, or nitinol.

While the larger ends of the coils are shown facing distally, that is not necessary. In an alternative embodiment, the larger coil ends can face proximally. Still further, one of the coils could have its larger end facing distally while another has its larger end facing proximally.

Referring back to the flowchart 92 shown in FIG. 22, after deployment of the fixation element into tissue, preferably in the lumbosacral fascial layer, the point-tip stylet 60 is removed 102 via the lead central lumen 41. To make sure there is no displacement of the stimulation lead during deployment of the fixation elements 66 and removal of the tube 72 or tube 73 and stylet 60, re-verification of lead position at the desired stimulation site should be repeated as described previously. Afterwards, a skin incision is made for implanting the neurostimulator, i.e., the implantable pulse generator (IPG). The lead proximal portion 38 is tunneled under the skin to bring it adjacent to the implanted IPG and then to the lead proximal connectors 52, 54, 56 and 58 are connected 106 to the appropriate IPG receptacles (not shown). After the IPG is activated, patient feedback is acquired to make sure the desired neural stimulation is achieved. Finally, the skin incisions for both the lead entry point and the IPG implant site are closed 108.

FIG. 23 shows a variation 94 of the preferred embodiment in FIG. 22 of the current invention. Instead of inserting a whole lead-stylet assembly 36, a needle similar to the stylet 60 and having a diameter much smaller than the assembly 36 is inserted first 110 to probe the desired stimulation site 112. Once the desired site is identified, the implant clinician records the needle depth and orientation as a reference, and the needle is removed. The recorded needle depth and orientation information is then used to guide insertion 96 of lead-stylet assembly 36. The remainder of the procedure steps are the same as in flowchart 92. However, comparing the flowcharts 92 and 94, it is seen that the latter enables an implant clinician to probe several sites with relatively more ease before implanting the lead assembly 36 than in the former. This helps reduce trauma to the patient and enhance therapy effectiveness.

Figure 16:
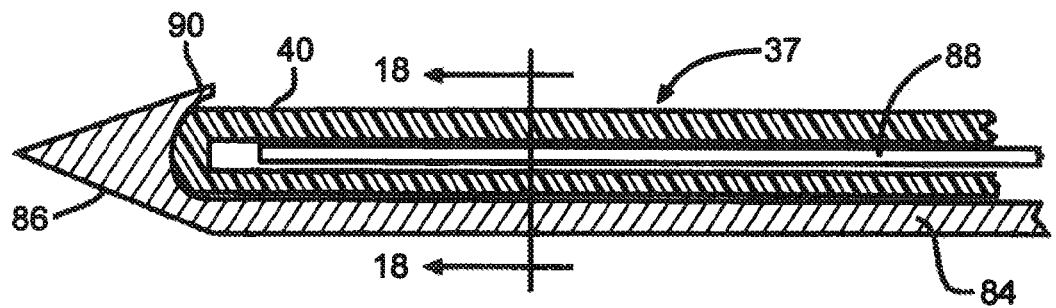
FIG. 16 shows a stimulation lead assembly having an elongated pointed-tip lead carrier.
Figure 17:
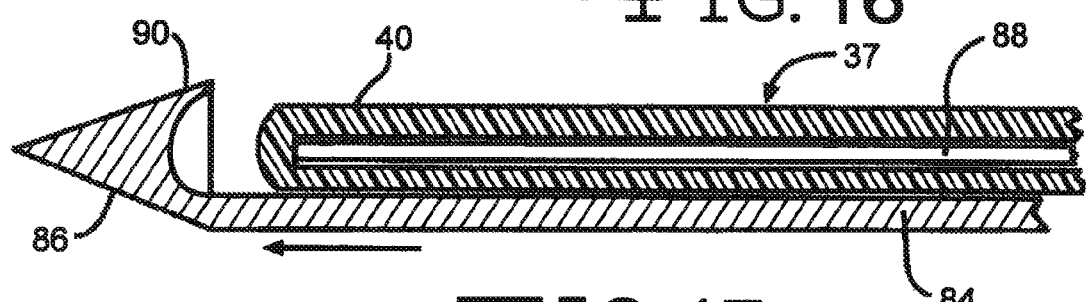
FIG. 17 shows a cross-sectional view of the lead assembly with the pointed-tip lead carrier disengaged from the lead.
Figure 18:
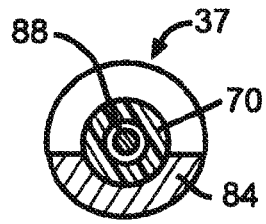
FIG. 18 is a cross-sectional view taken along line 18-18 of FIG. 16.

Another variation of the preferred embodiment of the lead-stylet assembly 36 is the implant assembly shown in FIGS. 16 and 17 having an elongated carrier body 84, a lead body 37 and a stylet 88. The lead body 37 has a central lumen 41, which does not run through to the lead tip. This means that the distal end of the stylet 88 within the lead body 37 is not exposed out from the distal end of the lead tip 40. In this embodiment, the carrier body 84 has a pointed tip 86 for cutting through tissue during implantation. The side wall of the carrier body 84 is sized to accommodate the lead body 37. With the lead body 37 nested in the carrier body, the lead tip 40 resides in a longitudinal cavity 90 extending along the distal end of the carrier.

Figure 19:
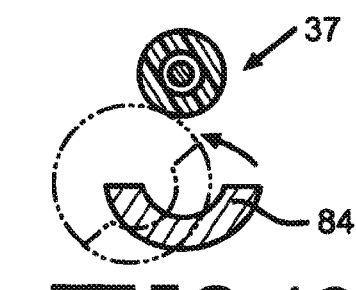
FIG. 19 shows a cross-sectional view of the disengagement of lead carrier from lead via rotation.
Figure 20:
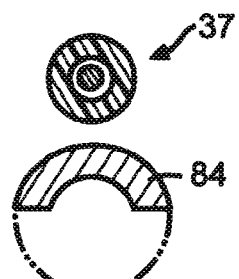
FIG. 20 shows a complete disengagement of the lead carrier from the lead after being rotated out of the way.
Figure 21:
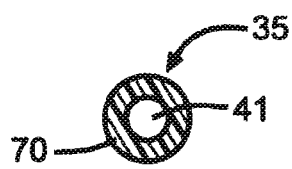
FIG. 21 shows a cross-sectional view of the lead after implantation, with both the stylet and the lead carrier removed from the implant site.

The distal end of the carrier 84 is then inserted into tissue in a similar manner as previously described with respect to the assembly 36. To disengage the carrier body 84 from the lead body 37, the clinician holds the lead body 37 and stylet 88 in place and pushes the carrier body 84 further forward, as shown by the arrow in FIG. 17. This caused the lead distal end 40 to separate from the carrier body cavity 90. To remove the carrier body 84 from the tissue, the carrier body 84 is rotated out of the way relative to the lead body 37 (FIG. 19). This ensures that the cavity 90 does not re-engage with the lead tip 40 during removal (FIG. 20). After the carrier body is removed, the lead is implanted into body tissue using either the previously described fixation fins 66 or the tapered coils. The stylet 88 is then removed, from the lead central lumen with only the stimulation lead 35 being left in place (FIG. 21).

Thus, embodiments of minimally invasive sacral lead implantation methods 92 and 94 are disclosed with many benefits. Embodiments of the methods can simplify the implant procedure, reduce trauma to the patient during implant procedure, reduce patient recovery time, and reduce healthcare costs. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A stimulation lead assembly, which comprises:
   a) lead, comprising:
      i) an elongated, insulated lead body comprising a first length extending from a proximal lead portion to a distal lead portion having a distal lead end;
      ii) at least one stimulation electrode at the distal lead portion;
      iii) at least one electrical connector at the proximal lead portion;
      iv) at least one conductor providing electrical continuity from the connector to the electrode; and
      v) at least one fixation finger attached to an outer surface of the lead body, wherein the fixation finger is deployable to secure the lead in body tissue; and
   b) an elongated lead carrier comprising:
      i) a carrier sidewall extending along a longitudinal axis from a proximal carrier porion to a distal carrier portion having a distal carrier pointed-tip; and
      ii) a longitudinal cavity that interrupts a portion of the carrier sidewall to provide a carrier nest for receiving the lead therein, wherein the carrier nest has a second length extending from a proximal nest portion adjacent to the proximal carrier portion to a distal nest end spaced proximally from the distal carrier pointed-tip,
      iii) wherein the carrier sidewall adjacent to the carrier nest has a first annular extent about the longitudinal axis and the carrier nest has a second annular extent that when combined with the first annular extent of the carrier sidewall equals 360 degrees, and
      iv) wherein the carrier distal pointed-tip extends annularly about the longitudinal axis,
   c) wherein the second length of the carrier nest in longer than the first length of the lead body so that with the lead received in the carrier nest, the carrier is manipulatable is a distal direction with respect to the lead to remove the distal pointed-tip from lateral alignment with the distal lead end so that the carrier is rotatable about the longitudinal axis and with respect to the lead to thereby separate the carrier from the lead so that the carrier is further manipulatable in a proximal direction to remove the carrier from the lead without causing proximal movement of the lead.

2. The lead assembly of claim 1 wherein the fixation finger has an attached end spaced from a free end, wherein the attachment end is secured to the outer surface of the lead body and the free end is movable from a first position closely spaced to the outer surface thereof to a second, deployed position spaced from the lead body a greater distance than that of the first position.

3. The lead assembly of claim 2 further comprising a tube that is sized to slide over the proximal lead portion and along the lead body outer surface to contact the at least one fixation finger to thereby move the finger from the second, deployed position into the first position, and wherein the tube is manipulatable in a proximal direction to remove the tube from contact with the finger and thereby enable the finger to move from the first position into the second, deployed position.

4. The lead assembly of claim 1 wherein the fixation finger has a finger length that is significantly longer that either one of a finger width or a finger diameter measured along a cross-section of the fixation finger perpendicular to the finger length.

5. The lead assembly of claim 1 wherein there are at least two fixation fingers, each finger having an end secured to the outer surface of the lead body and a free end that is movable from a first position closely spaced to the outer surface thereof to a second, deployed position spaced from the lead body a greater distance than that of the first position, and wherein a first distance from the distal lead end to where the attached end of a first one of the fingers is secured to the lead body is substantially different than a second distance measured from the distal lead end to where the attached end of the second one of the fingers is secured to the lead body.

6. The lead assembly of claim 5 further comprising a tube that is sized to slide over the outer surface of the lead body to contact the at least two fixation fingers and move them from the second, deployed position to the first position closely spaced to the outer surface of the lead body, and wherein the tube includes at least two longitudinal slots of different axial depths that correspond to the different distances that the two fixation fingers attached to the lead body are spaced from the distal, lead end so that the slots simultaneously contact the fixation fingers at different distances from the distal lead end when the tube is slid over the proximal lead portion toward the distal lead end.

7. The lead assembly of claim 1 wherein there are three fixation fingers, each finger having its respective attachment end secured to the lead body at a significantly different distance measured from the distal lead end than the other two fixation fingers.

8. The lead assembly of claim 1 wherein the lead body and the at least one fixation finger are of polymeric materials that are either the same or different and are selected from the group consisting of silicone, polyurethane, and mixtures thereof.

9. The lead assembly of claim 1 wherein a hollow lumen extends along at least a portion of the length of the lead body from the proximal lead end to the distal lead portion.

10. The lead assembly of claim 9 including a pointed-tip stylet sized to be housed inside the lumen extending through the lead body.

11. The lead assembly of claim 10 wherein the stylet has a third length that is longer than the first length of the lead body so that with a proximal end of the stylet detachably secured to a proximal end of the lead, a distal end of the stylet extends out past the distal lead end.

12. A stimulation lead assembly, which comprises:
a) a lead, comprising:
  i) an elongated, insulated lead body comprising a first length extending from a proximal lead portion to a distal lead portion having a distal lead end;
  ii) at least one stimulation electrode at the distal lead portion;
  iii) at least one electrical connector at the proximal lead portion;
  iv) at least one conductor providing electrical continuity from the connector to the electrode;
  v) a hollow lumen extending along the lead body from a proximal lead end to the distal lead portion; and
  vi) at least two fixation fingers, each finger having an end secured to the outer surface of the lead body and a free end that is movable from a first position closely spaced to the outer surface thereof to a second, deployed position spaced from the lead body a greater distance than that of the first position, and wherein a first distance from the distal lead end to where the attached end of a first one of the fingers is secured to the lead body is substantially different than a second distance measured from the distal lead end to where the attached end of the second one of the fingers is secured to the lead body;
b) a tube that is sized to slide over the outer surface of the lead body to contact the at least two fixation fingers and move them from the second, deployed position to the first position closely spaced to the outer surface of the lead body, wherein the tube includes at least two longitudinal slots of different axial depths that correspond to the different distances that the two fixation fingers attached to the lead body are spaced from the distal lead end so that the slots simultaneously contact the fixation fingers at different distances from the distal lead end when the tube is slid over the proximal lead portion toward the distal lead end; and
c) an elongated lead carrier comprising:
  i) a carrier sidewall extending along a longitudinal axis from a proximal carrier portion to a distal carrier portion having a distal carrier pointed-tip, and
  ii) a longitudinal cavity that interrupts a portion of the carrier sidewall to provide a carrier nest for receiving the lead therein, wherein the carrier nest has a second length extending from a proximal nest portion adjacent to the proximal carrier portion to a distal nest end spaced proximally the distal carrier pointed-tip,
  iii) wherein the carrier sidewall adjacent to the carrier nest has a first annular extent about the longitudinal axis and the carrier nest has a second annular extent that when combined with the first annular extent of the carrier sidewall equals 360 degrees, and
  iv) wherein the carrier distal pointed-tip extends annularly about the longitudinal axis,
d) wherein the second length of the carrier nest is longer than the first length of the lead body so that with the lead received in the carrier nest, the carrier is manipulatable in a distal direction with respect to the lead to remove the distal pointed-tip from lateral alignment with the distal lead end so that the carrier is rotatable about the longitudinal axis and with respect to the lead to thereby separate the carrier from the lead so that the carrier is further manipulatable in a proximal direction to remove the carrier from the lead without causing proximal movement of the lead.

13. The, lead assembly of claim 12 wherein each of the at least two fixation fingers has an attached end spaced from a free end, wherein the attachment end is secured to the outer surface of the lead body and the free end is movable from a first position closely spaced to the outer surface thereof to a second, deployed position spaced from the lead body a greater distance than that of the first position.

14. The lead assembly of claim 12 wherein the at least two fixation fingers each have a length that is significantly longer than either one of a finger width or a finger diameter measured along a cross-section of the fixation finger perpendicular to the finger length.

15. The lead assembly of claim 12 wherein the tube is manipulatable in a proximal direction to remove the tube from contact with the at least two fixation fingers and thereby enable the fingers to move from the first position into the second, deployed position.

16. The lead assembly of claim 12 wherein there are three fixation fingers, each having their respective attachment ends secured to the lead body at significantly different distances measured from the distal lead end than the other two fixation fingers.

17. The lead assembly of claim 12 wherein the lead body and the at least two fixation fingers are of polymeric materials that are either the same or different and are selected from the group consisting of silicone, polyurethane, and mixtures thereof.

18. A stimulation lead assembly, which comprises:
a) a lead, comprising:
  i) an elongated, insulated lead body extending from a proximal lead portion to a distal lead portion having a distal lead end;
  ii) at least one stimulation electrode at the distal lead portion;
  iii) at least one electrical connector at the proximal lead portion;

iv) at least one conductor providing electrical continuity from the connector to the electrode; and v) at least one fixation finger attached to an outer surface of the lead body, wherein the fixation finger is deployable to secure the lead in body tissue; and b) an elongated lead carrier comprising:

i) a carrier sidewall extending along a longitudinal axis from a proximal carrier portion to a distal carrier portion having a distal carrier pointed-tip; and ii) a longitudinal cavity that interrupts a portion of the carrier sidewall to provide a carrier nest for receiving the lead therein, wherein the carrier nest extends from a proximal nest portion adjacent to the proximal carrier portion to a distal nest end spaced proximally from the distal carrier pointed-tip, iii) wherein the carrier sidewall adjacent to the carrier nest has a first annular extent about the longitudinal axis and the carrier nest has a second annular extent that when combined with the first annular extent of the carrier sidewall equals 360 degrees, and iv) wherein the carrier distal pointed-tip extends annularly about the longitudinal axis, c) wherein the carrier is rotatable about the longitudinal axis and with respect to the lead to separate the carrier from the lead so that the carrier is manipulatable in a proximal direction to remove the carrier from the lead without causing proximal movement of the lead.

19. The lead assembly of claim 18 wherein there are at least two fixation fingers, each finger having an end secured to the outer surface of the lead body and a free end that is movable from a first position closely spaced to the outer surface thereof to a second, deployed position spaced from the lead body a greater distance than that of the first position, and wherein a first distance from the distal lead end to where the attached end of a first one of the fingers is secured to the lead body is substantially different than a second distance measured from the distal lead end to where the attached end of the second one of the fingers is secured to the lead body.

20. The lead assembly of claim 19 further comprising a tube that is sized to slide over the outer surface of the lead body to contact the at least two fixation fingers and move them from the second, deployed position to the first position closely spaced to the outer surface of the lead body, and wherein the tube includes at least two longitudinal slots of different axial depths that correspond to the different distances that the two fixation fingers attached to the lead body are spaced from the distal lead end so that the slots simultaneously contact the fixation fingers at different distances from the distal lead end when the tube is slid over the proximal lead portion toward the distal lead end.

* * * * *

UNITED STATES PATENT AND TRADEMARK OFFICE
CERTIFICATE OF CORRECTION

PATENT NO. : 8,781,603 B2  
APPLICATION NO. : 14/033592  
DATED : July 15, 2014  
INVENTOR(S) : Qingshan Ye and John M. Swoyer Page 1 of 1

It is certified that error appears in the above-identified patent and that said Letters Patent is hereby corrected as shown below:

In the Claims

Column 7, line 60 (Claim 1, line 2) after "a)" and before the word "lead" insert --a--

Column 8, line 25 (Claim 1, line 34) delete "is" and insert --in--

Column 8, line 51 (Claim 4, line 2) delete "that" and insert --than--

Column 9, line 7 (Claim 6, line 9) after the word "distal" delete the ","

Signed and Sealed this  
Seventeenth Day of March, 2015

Michelle K. Lee  
*Director of the United States Patent and Trademark Office*